(12) United States Patent
Gonzalez et al.

(10) Patent No.: US 8,778,826 B2
(45) Date of Patent: Jul. 15, 2014

(54) ENHANCED PROCATALYST COMPOSITION AND PROCESS

(75) Inventors: Kelly Gonzalez, Katy, TX (US); Clark C. Williams, Katy, TX (US); Linfeng Chen, Sugar Land, TX (US)

(73) Assignee: W. R. Grace & Co.-Conn., Columbia, MD (US)

( * ) Notice: Subject to any disclaimer, the term of this patent is extended or adjusted under 35 U.S.C. 154(b) by 125 days.

(21) Appl. No.: 12/651,032

(22) Filed: Dec. 31, 2009

(65) Prior Publication Data

US 2010/0173769 A1 Jul. 8, 2010

Related U.S. Application Data

(60) Provisional application No. 61/141,902, filed on Dec. 31, 2008, provisional application No. 61/141,959, filed on Dec. 31, 2008.

(51) Int. Cl.
*C08F 110/06* (2006.01)
*C08F 4/16* (2006.01)

(52) U.S. Cl.
USPC ........... 502/107; 502/103; 502/116; 502/118; 502/158; 526/351; 526/352; 526/65

(58) Field of Classification Search
USPC .................................. 526/123, 194
See application file for complete search history.

(56) References Cited

U.S. PATENT DOCUMENTS

| | | | |
|---|---|---|---|
| 4,442,276 A | 4/1984 | Kashiwa et al. | |
| 5,539,309 A | 7/1996 | Van Wyk et al. | |
| 6,420,499 B1 * | 7/2002 | Garoff et al. | 526/123.1 |
| 7,332,455 B2 | 2/2008 | Wei et al. | |
| 2005/0239636 A1 | 10/2005 | Gao et al. | |
| 2006/0264584 A1 * | 11/2006 | Wilson | 526/65 |
| 2009/0203863 A1 * | 8/2009 | Chen | 526/194 |

FOREIGN PATENT DOCUMENTS

| | | |
|---|---|---|
| WO | 03068828 A1 | 8/2003 |
| WO | 2010021762 A1 | 2/2010 |

* cited by examiner

*Primary Examiner* — Melvin C Mayes
*Assistant Examiner* — Colette Nguyen
(74) *Attorney, Agent, or Firm* — Lerner, David, Littenberg, Krumholz & Mentlik, LLP

(57) ABSTRACT

Disclosed herein are processes for preparing procatalyst compositions and polymers, i.e., propylene-based polymers, produced therefrom. The present procatalyst compositions improve catalyst selectivity and also increase the bulk density of the formant polymer.

10 Claims, No Drawings

ENHANCED PROCATALYST COMPOSITION AND PROCESS

PRIORITY CLAIM

This application claims priority to U.S. provisional application 61/141,902 filed on Dec. 31, 2008 and U.S. provisional application 61/141,959, filed on Dec. 31, 2008, the entire content of each application incorporated by reference herein.

BACKGROUND

The present disclosure relates to a process for enhancing procatalyst properties (selectivity) and/or formant polymer properties (bulk density). The present disclosure also relates to the improved procatalyst compositions and the improved formant polymers produced by these processes.

Worldwide demand for olefin-based polymers continues to grow as applications for these polymers become more diverse and more sophisticated. Known are Ziegler-Natta catalyst compositions for the production of olefin-based polymers. Ziegler-Natta catalyst compositions typically include a procatalyst containing a transition metal halide (i.e., titanium, chromium, vanadium), a cocatalyst such as an organoaluminum compound, and optionally an external electron donor. Ziegler-Natta catalyzed olefin-based polymers typically exhibit a narrow range of molecular weight distribution. Given the perennial emergence of new applications for olefin-based polymers, the art recognizes the need for olefin-based polymers with improved and varied properties.

Known are catalyst compositions containing a substituted phenylene aromatic diester as an internal electron donor used for the production of olefin-based polymers. Desirable would be Ziegler-Natta procatalyst compositions containing a substituted phenylene aromatic diester for the production of olefin-based polymers that provide high selectivity during polymerization. Further desired is a procatalyst composition that increases the bulk density of the formant polymer.

SUMMARY

The present disclosure provides a process. In an embodiment, a process is provided and includes halogenating a procatalyst precursor in the presence of a substituted phenylene aromatic diester at a temperature less than 115° C. The process also includes forming a procatalyst composition with a selectivity index of less than 2.5.

The disclosure provides another process. In an embodiment, a process is provided and includes first halogenating a procatalyst precursor in the presence of a substituted phenylene aromatic diester to form a procatalyst intermediate and second halogenating the procatalyst intermediate at a second temperature greater the first temperature. The process includes forming a procatalyst composition with a bulk density index from about 0.28 to about 0.5.

The disclosure provides a composition. In an embodiment, a procatalyst composition is provided and includes particles composed of a magnesium moiety, a titanium moiety, and an internal electron donor. The internal electron donor includes a substituted phenylene aromatic diester. The particles have a D50 from about 10 μm to about 25 μm.

An advantage of the present disclosure is the provision of an improved procatalyst composition.

An advantage of the present disclosure is the provision of a procatalyst composition with improved selectivity for the polymerization of olefin-based polymers.

An advantage of the present disclosure is the provision of a phthalate-free catalyst composition and a phthalate-free olefin-based polymer produced therefrom.

An advantage of the present disclosure is a catalyst composition that produces a propylene-based polymer with broad molecular weight distribution and/or high isotacticity.

An advantage of the present disclosure is a catalyst composition that increases the bulk density of the formant polymer particle.

DETAILED DESCRIPTION

The present disclosure provides a process for improving the selectivity of a procatalyst composition. The process includes lowering the reaction temperature during halogenation of a procatalyst precursor in the presence of a substituted phenylene aromatic diester. The lowered reaction temperature increases the selectivity of the procatalyst composition. The reaction temperature is lowered from a temperature greater than or equal to 115° C. to less than 115° C.

In an embodiment, a process is provided and includes halogenating a procatalyst precursor in the presence of a substituted phenylene aromatic diester. The halogenation is performed at a temperature less than 115° C., or from about 90° C. to less than or equal to 100° C. The process further includes forming a procatalyst composition with a selectivity index of less than 3.0, or less than 2.5. In an embodiment, the process includes forming a procatalyst composition having a selectivity index from 0.1 to less than 2.5.

The procatalyst precursor may be a magnesium moiety compound (MagMo), a mixed magnesium titanium compound (MagTi), or a benzoate-containing magnesium chloride compound (BenMag). In an embodiment, the procatalyst precursor is a magnesium moiety ("MagMo") precursor. The "MagMo precursor" contains magnesium as the sole metal component. The MagMo precursor includes a magnesium moiety. Nonlimiting examples of suitable magnesium moieties include anhydrous magnesium chloride and/or its alcohol adduct, magnesium alkoxide or aryloxide, mixed magnesium alkoxy halide, and/or carbonated magnesium dialkoxide or aryloxide. In one embodiment, the MagMo precursor is a magnesium di($C_{1-4}$)alkoxide. In a further embodiment, the MagMo precursor is diethoxymagnesium.

In an embodiment, the procatalyst precursor is a mixed magnesium/titanium compound ("MagTi"). The "MagTi precursor" has the formula $Mg_dTi(OR^e)_fX_g$ wherein $R^e$ is an aliphatic or aromatic hydrocarbon radical having 1 to 14 carbon atoms or COR' wherein R' is an aliphatic or aromatic hydrocarbon radical having 1 to 14 carbon atoms; each $OR^e$ group is the same or different; X is independently chlorine, bromine or iodine, preferably chlorine; d is 0.5 to 56, or 2 to 4; f is 2 to 116 or 5 to 15; and g is 0.5 to 116, or 1 to 3. The precursors are prepared by controlled precipitation through removal of an alcohol from the reaction mixture used in their preparation. In an embodiment, a reaction medium comprises a mixture of an aromatic liquid, especially a chlorinated aromatic compound, most especially chlorobenzene, with an alkanol, especially ethanol. Suitable halogenating agents include titanium tetrabromide, titanium tetrachloride or titanium trichloride, especially titanium tetrachloride. Removal of the alkanol from the solution used in the halogenation, results in precipitation of the solid precursor, having especially desirable morphology and surface area. Moreover, the resulting precursors are particularly uniform in particle size.

In an embodiment, the procatalyst precursor is a benzoate-containing magnesium chloride material. As used herein, a "benzoate-containing magnesium chloride" ("BenMag") can be a procatalyst (i.e., a halogenated procatalyst precursor) containing a benzoate internal electron donor. The BenMag material may also include a titanium moiety, such as a titanium halide. The benzoate internal donor is labile and can be replaced by other electron donors during procatalyst and/or catalyst synthesis. Nonlimiting examples of suitable benzoate groups include ethyl benzoate, methyl benzoate, ethyl p-methoxybenzoate, methyl p-ethoxybenzoate, ethyl p-ethoxybenzoate, ethyl p-chlorobenzoate. In one embodiment, the benzoate group is ethyl benzoate. Nonlimiting examples of suitable BenMag procatalyst precursors include catalysts of the trade names SHAC™ 103 and SHAC™ 310 available from The Dow Chemical Company, Midland, Mich. In an embodiment, the BenMag procatalyst precursor may be a product of halogenation of any procatalyst precursor (i.e., a MagMo precursor or a MagTi precursor) in the presence of a benzoate compound.

In an embodiment, the procatalyst precursor is synthesized so as to prepare procatalyst precursor particles having a D50 from about 5 µm to about 25 µm, or from about 10 µm to about 25 µm. The precursor preparation may also include a procedure whereby the particles are formed into rounded, smooth, spherical or substantially spherical (as opposed to jagged, rough or uneven) surface morphology. Subsequent halogenation and formation of the precursor into the procatalyst composition does not substantially change the D50 size range for the particles. Thus, the D50 for the procatalyst composition is also from about 5 µm to about 25 µm, or from about 10 µm to about 25 µm.

Halogenation of the procatalyst precursor occurs in the presence of an internal electron donor. As used herein, an "internal electron donor" (or "IED") is a compound added or otherwise formed during formation of the procatalyst composition that donates at least one pair of electrons to one or more metals present in the resultant procatalyst composition. The internal electron donor is a substituted phenylene aromatic diester. In an embodiment, the substituted phenylene aromatic diester is a phenylene aromatic diester and has the structure (I):

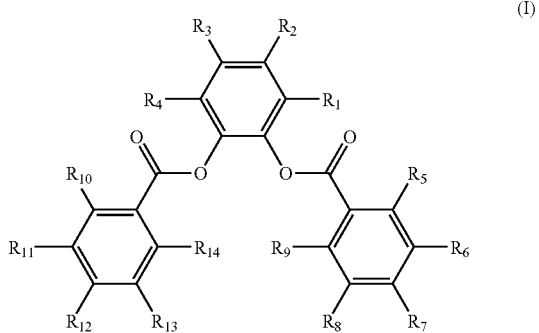

wherein $R_1$-$R_{14}$ are the same or different. Each of $R_1$-$R_{14}$ is selected from hydrogen, a halogen, a hydrocarbyl group having 1-20 carbon atoms and an alkoxy group having 1 to 20 carbon atoms, and combinations thereof. The hydrocarbyl group may be substituted or unsubstituted.

As used herein, the term "hydrocarbyl" or "hydrocarbon" is a substituent containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, alkylaryl-, and alkynyl-groups.

As used herein, the term "substituted hydrocarbyl" or "substituted hydrocarbon" is a hydrocarbyl group that is substituted with one or more nonhydrocarbyl substituent groups. A nonlimiting example of a nonhydrocarbyl substituent group is a heteroatom. As used herein, a "heteroatom" is an atom other than carbon or hydrogen. The heteroatom can be a non-carbon atom from Groups IV, V, VI, and VII of the Periodic Table. Nonlimiting examples of heteroatoms include: halogens (F Cl, Br, I), N, O, P, B, S, and Si. A substituted hydrocarbyl group also includes a halohydrocarbyl group and a silicon-containing hydrocarbyl group. As used herein, the term "halohydrocarbyl" group is a hydrocarbyl group that is substituted with one or more halogen atoms.

In an embodiment, the phenylene aromatic diester is a "substituted phenylene aromatic diester" wherein at least one of $R_1$-$R_{14}$ of structure (I) is not hydrogen. Nonlimiting examples of suitable substituted phenylene diester are found in Table 1 (in Examples section).

In an embodiment, the substituted phenylene aromatic diester is selected from 5-tert-butyl-3-methyl-1,2-phenylene dibenzoate and 4-tert-butyl-1,2-phenylene dibenzoate.

A "halogenating agent," as used herein, is a compound that converts the procatalyst precursor into a halide form. A "titanating agent," as used herein, is a compound that provides the catalytically active titanium species. Halogenation and titantation convert the magnesium moiety present in the procatalyst precursor into a magnesium halide support upon which the titanium moiety (such as a titanium halide) is deposited. Not wishing to be bound by any particular theory, it is believed that during halogenation and titanation the internal electron donor (1) regulates the formation of active sites and thereby enhances catalyst stereoselectivity, (2) regulates the position of titanium on the magnesium-based support, (3) facilitates conversion of the magnesium and titanium moieties into respective halides and (4) regulates the crystallite size of the magnesium halide support during conversion. Thus, provision of the internal electron donor yields a procatalyst composition with enhanced stereoselectivity.

In an embodiment, the halogenating agent is a titanium halide having the formula $Ti(OR^e)_f X_h$ wherein $R^e$ and X are defined as above, f is an integer from 0 to 3; h is an integer from 1 to 4; and f+h is 4. In this way, the titanium halide is simultaneously the halogenating agent and the titanating agent. In a further embodiment, the titanium halide is $TiCl_4$ and halogenation occurs by way of chlorination of the procatalyst precursor with the $TiCl_4$. The chlorination (and titanation) is conducted in the presence of a chlorinated or a non-chlorinated aromatic liquid, such as dichlorobenzene, o-chlorotoluene, chlorobenzene, benzene, toluene, or xylene. In yet another embodiment, the halogenation and the titanation are conducted by use of a mixture of halogenating agent and chlorinated aromatic liquid comprising from 40 to 60 volume percent halogenating agent, such as $TiCl_4$.

The procatalyst composition is chlorinated in the presence of the internal electron donor (i.e., the substituted phenylene aromatic diester) to form a reaction mixture which also contains a chlorinated aromatic compound. The reaction mixture is heated to a temperature less than 115° C., or from about 90° C. to less than or equal to 100° C. during chlorination. Applicants have surprisingly discovered that halogenation (i.e., chlorinating) of the procatalyst precursor and the substituted phenylene aromatic diester at a temperature range less than 115° C., and from 90° C. to less than or equal to 100° C. in particular, unexpectedly produces a procatalyst composition with improved selectivity. This result is unexpected because lowering the halogenation temperature during preparation of conventional procatalyst compositions reduces or otherwise diminishes procatalyst selectivity. In particular, it is known that reducing the halogenation temperature below 115° C. during preparation/halogenation of a phthalate-based internal electron donor (such as diisobutylphthalate) diminishes or otherwise degrades the selectivity for the phthalate-based procatalyst composition.

Unexpectedly, a halogentation temperature of less than 115° C. improves procatalyst selectivity when substituted phenylene dibenzoate is the internal electron donor. Not wishing to be bound by any particular theory, it is believed halogenation in the temperature range of less than 115° C., and from 90° C. to less than or equal to 100° C., (i) promotes formation of a magnesium moiety support populated with a titanium moiety while simultaneously (ii) preserving the structure of the substituted phenylene aromatic diester.

The foregoing processes improve procatalyst composition selectivity. The term "selectivity," (or "procatalyst selectivity") as used herein, is indicated by the amount of isotactic propylene homo-/co-polymer present in a sample of the polymer formed from the procatalyst composition. An "isotactic" polymer contains chiral centers with the same configuration. In contrast, "atactic" polymer has a random distribution of chiral centers with the same configuration.

The metric for procatalyst selectivity is the weight percent xylene solubles of a polymer sample formed from the procatalyst composition. The term "xylene solubles" (or "XS"), as used herein, is the fraction of polymer that is soluble in xylene at 25° C. The soluble fraction can be correlated to the amorphous fraction (i.e., the atactic fraction) in a propylene homo-/co-polymer. Isotactic propylene homo-/co-polymer is insoluble in xylene. Accordingly, the lower the weight percent of xylene solubles, the greater the amount of isotactic polymer present in the polymer sample and the greater the procatalyst selectivity.

In an embodiment, the procatalyst composition has a selectivity index. A "selectivity index," or "procatalyst selectivity index" is the weight % XS of a propylene-based polymer produced by the procatalyst composition. The procatalyst selectivity index connects or otherwise directly links the weight percent xylene solubles of the formant polymer with the procatalyst composition used to produce the polymer. The procatalyst selectivity index and the XS for the polymer are the same value. For example, a procatalyst selectivity index of 1.0 directly connects to the formant polymer having 1.0 wt % XS and vice versa. Thus, a procatalyst composition with a low selectivity index (i.e., formant polymer with low wt % XS) has high selectivity.

Procatalyst selectivity for two or more procatalyst compositions is evaluated under standard conditions. The term "standard conditions," as used herein, are reagent quantities and polymerization conditions that are the same (or substantially the same) across two or more polymerization reactions. As used herein, "polymerization conditions" are temperature, pressure, and reactor parameters within a polymerization reactor suitable for promoting polymerization between a catalyst composition (procatalyst and cocatalyst) and an olefin to form a desired polymer (ethylene is considered an olefin). The polymerization process may be a gas phase, a slurry, or a bulk polymerization process, operating in one, or more than one, polymerization reactor. Accordingly, the polymerization reactor may be a gas phase polymerization reactor, a liquid-phase polymerization reactor, or a combination thereof. It is understood that provision of hydrogen in the polymerization reactor is a component of the polymerization conditions. During polymerization, hydrogen is a chain transfer agent and affects the molecular weight (and correspondingly the melt flow rate) of the resultant polymer.

A nonlimiting example of polymerization performed under standard conditions includes introducing the same amount of procatalyst composition, cocatalyst, external electron donor, and olefin monomer (propylene) into two identical polymerization reactors (or the same polymerization reactor at different times) under the same, or substantially the same polymerization conditions (temperature, pressure, reactor type, and hydrogen concentration). Polymerization in each reactor is performed for the same time duration. XS is measured for the polymer formed in each reactor. In this way, polymerization under standard conditions enables the evaluation of the effect of procatalyst composition and/or procatalyst preparation upon procatalyst selectivity. It is understood that standard conditions can be used to evaluate the effects of other procatalyst/catalyst preparation techniques and/or other procatalyst components on the formant polymer (i.e., comparing procatalyst compositions with different internal electron donors and/or different procatalyst compositions) in a similar manner.

The foregoing processes advantageously reduce the amount of decomposition products present in the procatalyst composition. A "decomposition product," as used herein, is a compound formed from the decomposition of the internal electron donor during halogenation. Decomposition products include ethyl benzoate. In particular, the halogenation temperature range of less than 115° C., or from 90° C. to less than or equal to 100° C., advantageously maintains the compositional integrity of the substituted phenylene aromatic diester during procatalyst formation. Accordingly, an embodiment of the present process includes forming a procatalyst composition having an ethyl benzoate content from about 0 wt % to about 2.3 wt %, or from greater than 0 wt % to about 2.3 wt %. Weight percent is based on the total weight of the procatalyst composition. This contributes to improved procatalyst selectivity as will be explained below.

Ethoxide content in the procatalyst composition indicates the completeness of conversion of precursor metal ethoxide into a metal halide. The halogenation temperature range of less than 115° C., or from 90° C. to less than or equal to 100° C. does not inhibit conversion of ethoxide into halide during halogenation. In an embodiment, the process includes forming a procatalyst composition having from about 0.01 wt % to about 1.0 wt %, or from about 0.05 wt % to about 0.7 wt % ethoxide. Weight percent is based on the total weight of the procatalyst composition.

In an embodiment, the process includes forming a procatalyst composition (A) with a selectivity greater than the selectivity of a procatalyst composition (B). In other words, procatalyst (A) has a selectivity index that is less than the selectivity index of procatalyst (B). Procatalyst (B) is composed of the same procatalyst precursor and the same substituted phenylene aromatic diester as procatalyst (A). Halogenation of procatalyst (A) and procatalyst (B) is the same with the exception that halogenation of procatalyst (B) occurs at a temperature of 115° C. or greater. The process forms a procatalyst composition (A) with a selectivity index less than the selectivity index of a procatalyst composition (B). "Procatalyst (A)" is a procatalyst composition produced by any of the foregoing processes which includes a halogenation temperature of less than 115° C., or 90° C. to less than or equal to 100° C. "Procatalyst composition (B)" is a procatalyst composition containing the same procatalyst precursor and the same substituted phenylene aromatic diester as procatalyst composition (A). However, procatalyst composition (B) is halogenated at a temperature of 115° C. or greater. The present process which includes chlorination at a temperature of less than 115° C., or from about 90° C. to less than or equal to 100° C., advantageously improves the selectivity of the formed procatalyst composition.

In an embodiment, the present process forms a procatalyst composition (A) that produces 20-60% less xylene solubles in the formant polymer than the procatalyst composition (B). In an further embodiment, the process includes forming a procatalyst composition (A) having less decomposition products than procatalyst (B).

The present disclosure provides another process. In an embodiment, a process is provided and includes first halogenating a procatalyst precursor in the presence of a substituted phenylene aromatic diester at a first temperature (i.e., a first halogenation temperature). This forms a procatalyst intermediate. The process includes second halogenating the procatalyst intermediate at a second temperature (a second halogenation temperature). The second halogenation temperature is greater the first halogenation temperature. The process includes forming a procatalyst composition with a bulk density (BD) index from about 0.28 to about 0.5.

The term, "bulk density," (or "BD") as used herein, is the density of the polymer produced. Bulk density is determined by pouring the polymer resin through a standard powder funnel into a stainless standard cylinder and determining the weight of the resin for the given volume of the filled cylinder in accordance with ASTM D 1895B or equivalent. The "procatalyst bulk density index," or "bulk density index," or "BD index," is the bulk density value of a polymer produced by the procatalyst composition. The BD index connects or otherwise directly links the bulk density of the formant polymer with the procatalyst composition used to produce the polymer. Thus, the BD for the polymer and the BD index for the procatalyst composition are the same value. For example, a procatalyst composition with a BD index of 0.29 produces a polymer with a BD of 0.29 g/cc.

In an embodiment, the substituted phenylene aromatic diester for the first halogenation is selected from 5-tert-butyl-3-methyl-1,2 phynylene dibenzoate and/or 4-tert-butyl-1,2-phenylene dibenzoate.

In an embodiment, the first halogenation is performed at a temperature less than 115° C., or from 90° C. to 100° C., and the second halogenation is performed at a temperature greater than or equal to 115° C., or 130° C.

In an embodiment, the second halogenation of the procatalyst intermediate is performed in the presence of a substituted phenylene aromatic diester. The substituted phenylene aromatic diester may be the same or different than the substituted phenylene aromatic diester in the first halogenation. In a further embodiment, the substituted phenylene aromatic diester present during the second halogenation is 5-tert-butyl-3-methyl-1,2-phenylene dibenzoate and/or 4-tert-butyl-1,2-phenylene dibenzoate.

In an embodiment, the process includes third halogenating the procatalyst intermediate. The third halogenation is performed at a temperature greater than the first temperature, or from greater than 115° C. to 130° C., or 130° C. The third halogenation may or may not be performed in the presence of a substituted phenylene aromatic diester.

In an embodiment, the process includes forming a procatalyst composition comprising from 0 wt % to less than 2.3 wt % or greater than 0 wt % to less than 2.3 wt % decomposition product.

In an embodiment, the bulk density (BD) of two or more polymers (or the BD index of two or more procatalyst compositions) is evaluated under standard conditions. A nonlimiting example of a BD determination performed under standard conditions includes introducing the same amount of procatalyst composition, cocatalyst, external electron donor, and olefin monomer (such as propylene) into two identical polymerization reactors (or sequential polymerization in the same reactor at different times) under the same, or substantially the same polymerization conditions (temperature, pressure, reactor type, and hydrogen concentration). Polymerization in each reactor is performed for the same time duration. Formant polymer particles are retrieved from each reactor run and the bulk density is measured. From the bulk density measurement, an BD index is determined or otherwise identified for each procatalyst composition. In this way, standard conditions permit the evaluation of the effect(s) procatalyst preparation and/or a change in procatalyst/catalyst component on the bulk density of the formant polymer.

In an embodiment, the process includes forming a procatalyst composition (C) with a bulk density (BD) index greater than the BD index of a procatalyst composition (D). "Procatalyst (C)" is a procatalyst composition produced by at least two halogenation procedures whereby the second halogenation temperature is greater than the first halogenation temperature as disclosed above. "Procatalyst composition (D)" is a procatalyst composition containing the same procatalyst precursor and the same substituted phenylene aromatic diester as procatalyst composition (C). However, procatalyst composition (D) is halogenated by at least two halogenation procedures, the temperature for each halogenation being the same or substantially the same. The present process which includes a second halogenation temperature greater than the first halogenation temperature advantageously increases the bulk density of the formant polymer (i.e., a greater BD index for procatalyst composition (C) compared to the BD of the formant polymer from procatalyst (D).

In an embodiment, the procatalyst composition (C) has a selectivity index less than the selectivity index of procatalyst composition (D) at standard conditions. In other words, under standard conditions, the procatalyst composition (C) produces a propylene-based polymer with less xylene solubles than the propylene-based polymer produced by procatalyst (D). In a further embodiment, the process includes contacting, under polymerization conditions, the procatalyst composition (C), a cocatalyst, and an external electron donor with propylene and optionally one or more olefins in a polymerization reactor, and forming a propylene-based polymer having (i) less than 4 wt %, or less than 3 wt %, or from 0.5 wt % to less than 2.5 wt %, xylene solubles and/or (ii) particles of the propylene-based polymer with a bulk density greater than 0.28 g/cc to about 0.5 g/cc.

In any of the foregoing processes, the procatalyst composition may be rinsed or washed with a liquid diluent to remove unreacted $TiCl_4$ and may be dried to remove residual liquid, after or between halogenation steps. Typically the resultant solid procatalyst composition is washed one or more times with a "wash liquid," which is a liquid hydrocarbon such as an aliphatic hydrocarbon such as isopentane, isooctane, isohexane, hexane, pentane, or octane. Not wishing to be bound by any particular theory, it is believed that (1) further halogenation and/or (2) further washing results in desirable modification of the procatalyst composition, possibly by removal of certain inactive metal compounds that are soluble in the foregoing diluent.

The resulting procatalyst composition from any of the foregoing processes has a titanium content of from about 1.0 percent by weight to about 6.0 percent by weight, based on the total solids weight, or from about 1.5 percent by weight to about 5.5 percent by weight, or from about 2.0 percent by weight to about 5.0 percent by weight. The weight ratio of titanium to magnesium in the solid procatalyst composition is suitably between about 1:3 and about 1:160, or between about 1:4 and about 1:50, or between about 1:6 and 1:30. The internal electron donor is present in an amount from about 0.1 wt % to about 30.0 wt %, or from about 1.0 wt % to about 30 wt %. The internal electron donor may be present in the procatalyst composition in a molar ratio of internal electron donor to magnesium of from about 0.005:1 to about 1:1, or from about 0.01:1 to about 0.4:1. Weight percent is based on the total weight of the procatalyst composition.

Applicants have surprisingly discovered that lowering the temperature during the first halogenation alone or in combination with increasing the temperature during subsequent halogenations unexpectedly (1) improves the procatalyst selectivity index (i.e., lower xylene solubles in the formed polymer) (2) produces a procatalyst composition with a low amount of, or no, or substantially no, decomposition products, and (3) increases the procatalyst bulk density index (i.e., increases the BD of the formant polymer).

Bounded by no particular theory, it is believed that the different responses to temperature is due to higher concentration of titanium alkoxide byproducts in the first halogenation reaction compared to the subsequent halogenations. The titanium alkoxide byproducts react with the substituted phenylene aromatic diester. Lowering the first halogenation temperature slows this reaction and preserves the substituted phenylene aromatic diester. After the first halogenation, the concentration of titanium alkoxide byproducts is less than during the first halogenation. Raising the halogenation temperature after the first halogenation does not lead to internal electron donor side reactions with the titanium alkoxide byproducts. Thus, raising the halogenation temperature after the first halogenation promotes halogenation and improves (i.e., increases) the bulk density index for the procatalyst composition.

Any of the foregoing processes may comprise two or more embodiments.

The present disclosure provides a procatalyst composition. In an embodiment, particles of a procatalyst composition are provided. The procatalyst composition particles include a magnesium moiety, a titanium moiety, and an internal electron donor. The internal electron donor is any substituted phenylene aromatic diester as disclosed herein. The procatalyst composition particles have a D50 from about 1 μm to about 50 μm, or from about 5 nm to about 25 μm or from about 10 μm to about 25 μm. As used herein "D50" is the particle diameter such that 50% of the sample weight is above the stated particle diameter.

Applicants have surprisingly discovered that reducing the particle size of the procatalyst composition unexpectedly increases the procatalyst bulk density index (i.e., increases the bulk density for the formant polymer), and does so without increasing the level of polymer particles less than 250 μm in diameter. In an embodiment, the procatalyst composition with a D50 particle size from 5 μm to about 25 μm has a procatalyst bulk density index greater than 0.26, or greater than 0.28 to about 0.50.

The internal electron donor is a substituted phenylene aromatic diester. In an embodiment, the substituted phenylene aromatic diester is a substituted phenylene aromatic diester such as 5-tert-butyl-3-methyl-1,2-phenylene dibenzoate (IED1) and/or 4-tert-butyl-1,2-phenylene dibenzoate (IED2). The procatalyst composition contains less than 2.3 wt %, or from 0 wt % to less than 2.3 wt %, or from greater than 0 wt % to less than 2.3 wt % ethyl benzoate.

In an embodiment, the substituted phenylene aromatic diester is a phenylene dibenzoate and the procatalyst composition contains from about 0.1 wt % to about 30 wt % of the phenylene dibenzoate.

In an embodiment, the magnesium moiety is a magnesium chloride. The titanium moiety is a titanium chloride.

The procatalyst composition may comprise two or more embodiments disclosed herein.

Any of the foregoing procatalyst compositions may be used in a polymerization process. In an embodiment, a polymerization process is provided and includes contacting, under polymerization conditions, the procatalyst composition composed of substituted phenylene aromatic diester (such as procatalyst (A) and/or (C)), a cocatalyst, optionally an external electron donor with propylene and optionally one or more olefins. The polymerization forms a propylene-based polymer having less than 4 wt %, or less than 3 wt %, or less than 2.5 wt %, or less than 1 wt %, or from 0.1 wt % to less than 4 wt %, or from 0.1 wt % to less than 2.5 wt % xylene solubles. Weight percent XS is based on the total weight of the polymer.

As used herein, a "cocatalyst" is a substance capable of converting the procatalyst to an active polymerization catalyst. The cocatalyst may include hydrides, alkyls, or aryls of aluminum, lithium, zinc, tin, cadmium, beryllium, magnesium, and combinations thereof. In an embodiment, the cocatalyst is a hydrocarbyl aluminum compound represented by the formula $R_nAlX_{3-n}$, wherein n=1 2, or 3, R is an alkyl, and X is a halide or alkoxide. In an embodiment, the cocatalyst is selected from trimethylaluminum, triethylaluminum, triisobutylaluminum, and tri-n-hexylaluminum.

Nonlimiting examples of suitable hydrocarbyl aluminum compounds are as follows: methylaluminoxane, isobutylaluminoxane, diethylaluminum ethoxide, diisobutylaluminum chloride, tetraethyldialuminoxane, tetraisobutyldialuminoxane, diethylaluminum chloride, ethylaluminum dichloride, methylaluminum dichloride, dimethylaluminum chloride, triisobutylaluminum, tri-n-hexylaluminum, diisobutylaluminum hydride, di-n-hexylaluminum hydride, isobutylaluminum dihydride, n-hexylaluminum dihydride, diisobutylhexylaluminum, isobutyldihexylaluminum, trimethylaluminum, triethylaluminum, tri-n-propylaluminum, triisopropylaluminum, tri-n-butylaluminum, tri-n-octylaluminum, tri-n-decylaluminum, tri-n-dodecylaluminum, diisobutylaluminum hydride, and di-n-hexylaluminum hydride.

In an embodiment, the cocatalyst is triethylaluminum. The molar ratio of aluminum to titanium is from about 5:1 to about 500:1, or from about 10:1 to about 200:1, or from about 15:1 to about 150:1, or from about 20:1 to about 100:1. In another embodiment, the molar ratio of aluminum to titanium is about 45:1.

As used herein, an "external electron donor" (or "EED") is a compound added independent of procatalyst formation and includes at least one functional group that is capable of donating a pair of electrons to a metal atom. Bounded by no particular theory, it is believed that provision of one or more external electron donors in the catalyst composition affects the following properties of the formant polymer: level of tacticity (i.e., xylene soluble material), molecular weight (i.e., melt flow), molecular weight distribution (MWD), melting point, and/or oligomer level.

In an embodiment, the EED is a silicon compound having the general formula (II):

$$SiR_m(OR')_{4-m} \qquad (II)$$

wherein R independently each occurrence is hydrogen or a hydrocarbyl or an amino group, optionally substituted with one or more substituents containing one or more Group 14, 15, 16, or 17 heteroatoms. R contains up to 20 atoms not counting hydrogen and halogen. R' is a $C_{1-20}$ alkyl group, and m is 0, 1, 2, or 3. In an embodiment, R is $C_{6-12}$ aryl, alkyl or alkylaryl, $C_{3-12}$ cycloalkyl, $C_{3-12}$ branched alkyl, or $C_{3-12}$ cyclic amino group, R' is $C_{1-4}$alkyl, and m is 1 or 2.

In an embodiment, the silane composition is dicyclopentyldimethoxysilane (DCPDMS), methylcyclohexyldimethoxysilane (MChDMS), or n-propyltrimethoxysilane (NPTMS), and any combination thereof.

The polymerization reaction forms a propylene homopolymer or a propylene copolymer. Optionally, one or more olefin monomers can be introduced into a polymerization reactor along with the propylene to react with the procatalyst, cocatalyst, and EED and to form a polymer, or a fluidized bed of polymer particles. Nonlimiting examples of suitable olefin monomers include ethylene, $C_{4-20}$ α-olefins, such as 1-butene, 1-pentene, 1-hexene, 4-methyl-1-pentene, 1-heptene, 1-octene, 1-decene, 1-dodecene and the like.

In an embodiment, the polymerization process may include a pre-polymerization step and/or a pre-activation step.

In an embodiment, the process includes mixing the external electron donor with the procatalyst composition. The external electron donor can be complexed with the cocatalyst and mixed with the procatalyst composition (pre-mixed) prior to contact between the catalyst composition and the olefin. In another embodiment, the external electron donor can be added independently to the polymerization reactor.

In an embodiment, the process includes forming a propylene-based polymer (propylene homopolymer or propylene copolymer) containing the substituted phenylene aromatic diester (i.e., containing 5-tert-butyl-3-methyl-1,2-phenylene dibenzoate and/or 4-tert-butyl-1,2-phenylene dibenzoate). The propylene-based polymer has one or more of the following properties:
- a melt flow rate (MFR) from about 0.01 g/10 min to about 800 g/10 min, or from about 0.1 g/10 min to about 200 g/10 min, or from about 0.5 g/10 min to about 150 g/10 min;
- a xylene solubles content from about 0.1% to about 10%, or from about 0.1% to about 8%, or from about 0.1% to about 4%, or from about 0.1% to less than 2.5%;
- a polydispersity index (PDI) from about 3.8 to about 15.0, or from about 4.0 to about 10, or from about 4.0 to about 8.0; and/or
- particles thereof with a bulk density greater than 0.28 g/cc to about 0.50 g/cc.

The propylene-based polymer may comprise two or more embodiments disclosed herein.

In an embodiment, the procatalyst composition and/or the polymer produced therefrom are/is phthalate-free or are/is otherwise void or devoid of phthalate and derivatives thereof.

Definitions

All references to the Periodic Table of the Elements herein shall refer to the Periodic Table of the Elements, published and copyrighted by CRC Press, Inc., 2003. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 to 20 carbon atoms.

The term "alkylaryl" or "alkylaryl group," as used herein, is an alkyl group substituted by at least one aryl group.

The term "aryl" or "aryl group," as used herein, is a substituent derived from an aromatic hydrocarbon compound. An aryl group has a total of from six to twenty ring atoms, and has one or more rings which are separate or fused, and may be substituted with alkyl and/or halo groups. The aromatic ring(s) may include phenyl, naphthyl, anthracenyl, and biphenyl, among others.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term "polymer" is a macromolecular compound prepared by polymerizing monomers of the same or different type. "Polymer" includes homopolymers, copolymers, terpolymers, interpolymers, and so on. The term "interpolymer" is a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term, "propylene-based polymer," as used herein, is a polymer that comprises a majority weight percent polymerized propylene monomer (based on the total amount of polymerizable monomers), and optionally may comprise at least one polymerized comonomer.

The term "substituted alkyl," as used herein, is an alkyl as previously defined described in which one or more hydrogen atoms bound to any carbon of the alkyl is replaced by another group such as a halogen, aryl, substituted aryl, cycloalkyl, substituted cycloalkyl, heterocycloalkyl, substituted heterocycloalkyl, haloalkyl, hydroxy, amino, phosphido, alkoxy, thio, nitro, and combinations thereof. Suitable substituted alkyls include, for example, benzyl, trifluoromethyl and the like.

Test Methods

Melt flow rate (MFR) is measured in accordance with ASTM D 1238-01 test method at 230° C. with a 2.16 kg weight for propylene-based polymers.

Xylene Solubles (XS) is the weight percent of resin (based on the total weight of the resin) that stays in the solution after the resin is dissolved in hot xylene and the solution is allowed to cool to 25° C. XS is measured using a $^1$H NMR method as described in U.S. Pat. No. 5,539,309, the entire content of which is incorporated herein by reference. XS may also be measured by flow injection polymer analysis using a Viscotek ViscoGEL H-100-3078 column with THF mobile phase flowing at 1.0 ml/min. The column is coupled to a Viscotek Model 302 Triple Detector Array, with light scattering, viscometer and refractometer detectors operating at 45° C. Instrument calibration is maintained with Viscotek PolyCAL™ polystyrene standards.

Polydispersity Index (PDI) is measured by an AR-G2 rheometer, which is a stress control dynamic spectrometer manufactured by TA Instruments, using a method according to Zeichner G R, Patel P D (1981) "A comprehensive Study of Polypropylene Melt Rheology" Proc. of the $2^{nd}$ World Congress of Chemical Eng., Montreal, Canada. An ETC oven is used to control the temperature at 180° C.±0.1° C. Nitrogen is used to purge the inside of the oven to protect the sample from degradation by oxygen and moisture. A pair of 25 mm diameter cone and plate sample holders is used. Samples are compression molded into 50 mm×100 mm×2 mm plaques. Each sample is then cut into a 19 mm square and loaded onto the center of the bottom plate. The geometries of upper cone are (1) Cone angle: 5:42:20 (deg:min:sec); (2) Diameter: 25 mm; (3) Truncation gap: 149 micron. The geometry of the bottom plate is a 25 mm circle.

Testing procedure:
(1) The cone & plate sample holder is heated in the ETC oven at 180° C. for 10 minutes. Then the gap is zeroed under a blanket of nitrogen gas.
(2) The Cone is raised to 2.5 mm and the sample is loaded onto the top of the plate.
(3) The timer is set for 2 minutes.
(4) The upper cone is immediately lowered to slightly rest on top of the sample by observing the normal force.
(5) After two minutes the sample is squeezed down to a 165 micron gap by lowering the upper cone.
(6) The normal force is observed. When the normal force is down to <0.05 Newton, the excess sample is removed from the edge of the cone and plate sample holder using a spatula.
(7) The upper cone is lowered again to the truncation gap which is 149 micron.
(8) An Oscillatory Frequency Sweep test is performed under these conditions:
 (i) Test delayed at 180° C. for 5 minutes.
 (ii) Frequencies: 628.3r/s to 0.1r/s.
 (iii) Data acquisition rate: 5 point/decade.
 (iv) Strain: 10%
(9) When the test is complete, the crossover modulus (Gc) is detected by the Rheology Advantage Data Analysis program furnished by TA Instruments.
(10) PDI=100,000÷Gc (in Pa units).

Final melting point ($T_{MF}$) is the temperature to melt the most perfect crystal in the sample and is a measure for isotacticity and inherent polymer crystallizability. The test is conducted using a TA Q100 Differential Scanning Calorimeter. A sample is heated from 0° C. to 240° C. at a rate of 80° C./min, cooled at the same rate to 0° C., then heated again at the same rate up to 150° C., held at 150° C. for 5 minutes and the heated from 150° C. to 180° C. at 1.25° C./min. The $T_{MF}$ is determined from this last cycle by calculating the onset of the baseline at the end of the heating curve.

Testing procedure:
(1) Calibrate instrument with high purity indium as standard.
(2) Purge the instrument head/cell with a constant 50 ml/min flow rate of nitrogen.
(3) Sample preparation:
 Compression mold 1.5 g of powder sample using a 30-G302H-18-CX Wabash Compression Molder (30 ton): (a) heat mixture at 230° C. for 2 minutes at contact; (b) compress the sample at the same temperature with 20 ton pressure for 1 minute; (c) cool the sample to 45° F. and hold for 2 minutes with 20 ton pressure; (d) cut the plaque into 4 plaques of about the same size, stack them together, and then repeat steps (a)-(c) in order to homogenize the sample.
(4) Weigh a piece of sample (preferably between 5 to 8 mg) from the sample plaque and seal it in a standard aluminum sample pan. Place the sealed pan containing the sample on the sample side of the instrument head/cell and place an empty sealed pan in the reference side. If using the auto sampler, weigh out several different sample specimens and set up the machine for a sequence.
(5) Measurements:
 (i) Data storage: off
 (ii) Ramp 80.00° C./min to 240.00° C.
 (iii) Isothermal for 1.00 min
 (iv) Ramp 80.00° C./min to 0.00° C.
 (v) Isothermal for 1.00 min (vi) Ramp 80.00° C./min to 150.00° C.
(vii) Isothermal for 5.00 min
(viii) Data storage: on
(ix) Ramp 1.25° C./min to 180.00° C.
(x) End of method
(6) Calculation: $T_{MF}$ is determined by the interception of two lines. Draw one line from the base-line of the high temperature region of the enthalpy curve. Draw another line through the inflection point of the high-temperature side of the enthalpy curve. The $T_{MF}$ is the temperature at which the two lines intersect.

By way of example and not by limitation, examples of the present disclosure will now be provided.

EXAMPLES

I. Internal Electron Donor

Nonlimiting examples of substituted phenylene aromatic diesters suitable for the internal electron donor are the substituted phenylene aromatic dibenzoates provided in Table 1 below.

TABLE 1

| Compound | Structure | $^1$H NMR (500 MHz, CDCl$_3$, ppm) |
|---|---|---|
| 3-methyl-5-tert-butyl-1,2-phenylene dibenzoate (IED1) | 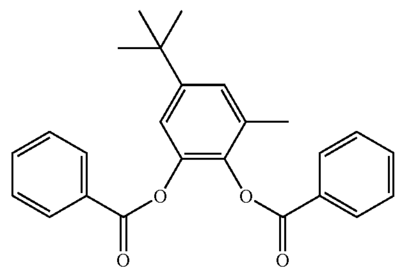 [SMILES: Cc1cc(C(C)(C)C)cc(OC(=O)c2ccccc2)c1OC(=O)c1ccccc1] | 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H). |
| 3-tert-butyl-5-methyl-1,2-phenylene dibenzoate | 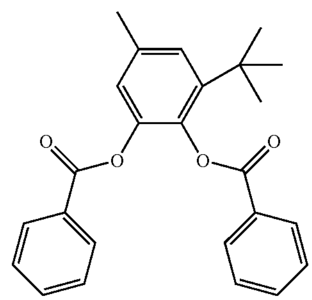 [SMILES: Cc1cc(OC(=O)c2ccccc2)c(OC(=O)c2ccccc2)c(C(C)(C)C)c1] | 8.08 (dd, 2H), 7.93 (dd, 2H), 7.53 (tt, 1H), 7.43 (tt, 1H), 7.38 (t, 2H), 7.25 (t, 2H), 7.16 (d, 1H), 7.11 (d, 1H), 2.41 (s, 3H), 1.38 (s, 9H). |
| 3,5-di-tert-butyl-1,2-phenylene dibenzoate | 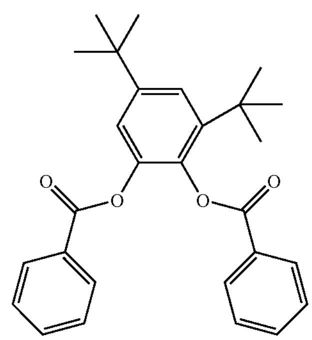 [SMILES: CC(C)(C)c1cc(OC(=O)c2ccccc2)c(OC(=O)c2ccccc2)c(C(C)(C)C)c1] | 8.08 (dd, 2H), 7.94 (dd, 2H), 7.52 (tt, 1H), 7.44 (tt, 1H), 7.36-7.40 (m, 3H), 7.23-7.27 (m, 3H), 1.40 (s, 9H), 1.38 (s, 9H). |
| 3,5-diisopropyl-1,2-phenylene dibenzoate | 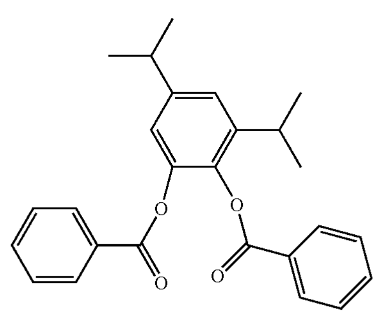 [SMILES: CC(C)c1cc(OC(=O)c2ccccc2)c(OC(=O)c2ccccc2)c(C(C)C)c1] | 8.08 (dd, 2H), 7.00 (dd, 2H), 7.53 (tt, 1H), 7.48 (tt, 1H), 7.39 (t, 2H), 7.31 (t, 2H), 7.11 (d, 1H), 7.09 (d, 1H), 3.11 (heptat, 1H), 2.96 (heptat, 1H), 1.30 (d, 6H), 1.26 (d, 6H). |

TABLE 1-continued

| Compound | Structure | ¹H NMR (500 MHz, CDCl₃, ppm) |
|---|---|---|
| 3,6-dimethyl-1,2-phenylene dibenzoate | 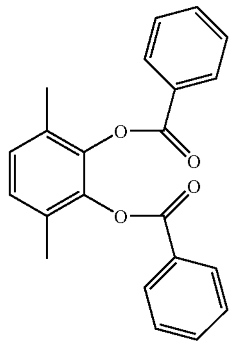 [SMILES: Cc1ccc(C)c(OC(=O)c2ccccc2)c1OC(=O)c1ccccc1] | 8.08 (d, 2H), 7.51 (t, 1H), 7.34 (d, 2H), 7.11 (s, 2H), 2.23 (s, 6H). |
| 4-t-butyl-1,2-phenylene dibenzoate (IED2) | 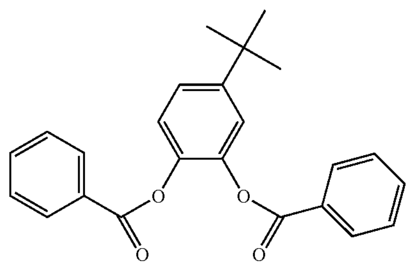 [SMILES: CC(C)(C)c1ccc(OC(=O)c2ccccc2)c(OC(=O)c2ccccc2)c1] | 8.07 (dd, 4H), 7.54 (m, 2H), 7.30-7.40 (m, 7H), 1.37 (s, 9H). |
| 4-methyl 1,2-phenylene dibenzoate | 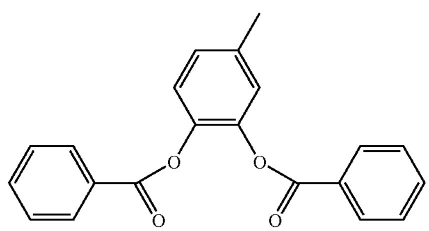 [SMILES: Cc1ccc(OC(=O)c2ccccc2)c(OC(=O)c2ccccc2)c1] | 8.07 (d, 4H), 7.54 (t, 2H), 7.37 (t, 4H), 7.27 (d, 1H), 7.21 (s, 1H), 7.15 (d, 1H), 2.42 (s, 3H). |
| 1,2-naphthalene dibenzoate | 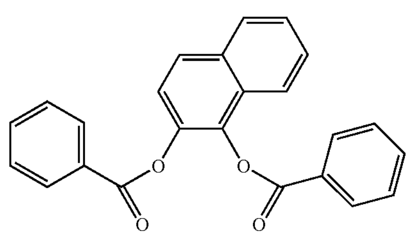 [SMILES: O=C(Oc1ccc2ccccc2c1OC(=O)c1ccccc1)c1ccccc1] | 8.21-8.24 (m, 2H), 8.08-8.12 (m, 2H), 7.90-7.96 (m, 2H), 7.86 (d, 1H), 7.60 (m, 1H), 7.50-7.55 (m, 4H), 7.46 (t, 2H), 7.37 (t, 2H). |
| 2,3-naphthalene dibenzoate | 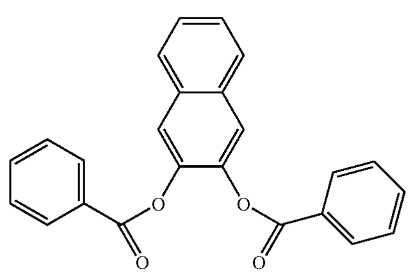 [SMILES: O=C(Oc1cc2ccccc2cc1OC(=O)c1ccccc1)c1ccccc1] | 8.08-8.12 (m, 4H), 7.86-7.90 (m, 4H), 7.51-7.58 (m, 4H), 7.38 (t, 4H) |

TABLE 1-continued

| Compound | Structure | $^1$H NMR (500 MHz, CDCl$_3$, ppm) |
|---|---|---|
| 3-methyl-5-tert-butyl-1,2-phenylene di(4-methylbenzoate) | | 7.98 (d, 2H), 7.93 (d, 2H), 7.18 (d, 4H), 7.15 (d, 2H), 2.38 (s, 3H), 2.36 (s, 3H), 2.26 (s, 3H), 1.35 (s, 9H). |
| 3-methyl-5-tert-butyl-1,2-phenylene di(2,4,6-trimethylbenzoate) | 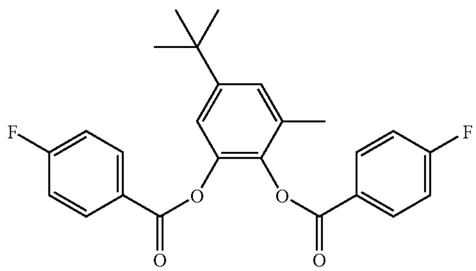 [SMILES: Cc1cc(C(C)(C)C)cc(OC(=O)c2ccc(F)cc2)c1OC(=O)c1ccc(F)cc1] | 7.25 (s, 1H), 7.21 (s, 1H), 6.81 (d, 4H), 2.36 (s, 3H), 2.30 (d, 6H), 2.25 (s, 6H), 2.23 (s, 6H), 1.36 (s, 9H). |
| 3-methyl-5-tert-butyl-1,2-phenylene di(4-fluorobenzoate) | 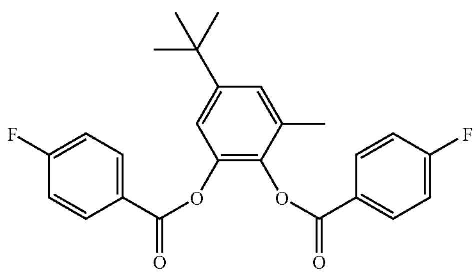 [SMILES: Cc1cc(C(C)(C)C)cc(OC(=O)c2ccc(F)cc2)c1OC(=O)c1ccc(F)cc1] | 7.98 (dd, 4H), 7.36 (dd, 4H), 7.21 (s, 1H), 7.17 (s, 1H), 2.26 (s, 3H), 1.34 (s, 9H). |
| 3,6-dichloro-1,2-phenylene dibenzoate | 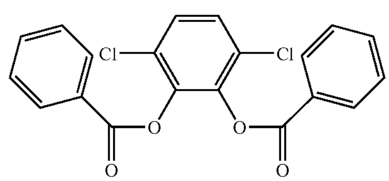 [SMILES: O=C(Oc1c(Cl)ccc(Cl)c1OC(=O)c1ccccc1)c1ccccc1] | 8.10 (d, 2H), 7.57 (t, 1H), 7.41 (d, 2H), 7.49 (s, 2H). |
| 3-methyl-5-tert-butyl-1,2-phenylene di(4-chlorobenzoate) | 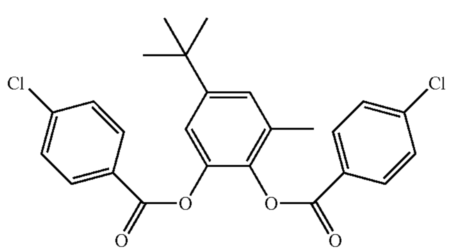 [SMILES: Cc1cc(C(C)(C)C)cc(OC(=O)c2ccc(Cl)cc2)c1OC(=O)c1ccc(Cl)cc1] | 7.98 (dd, 4H), 7.36 (dd, 4H), 7.21 (s, 1H), 7.17 (s, 1H), 2.26 (s, 3H), 1.34 (s, 9H). |
| 3-methyl-5-tert-butyl-1,2-phenylene di(1-naphthoate) | 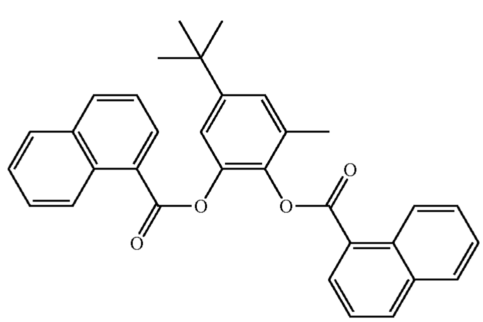 [SMILES: Cc1cc(C(C)(C)C)cc(OC(=O)c2cccc3ccccc23)c1OC(=O)c1cccc2ccccc12] | |

TABLE 1-continued

| Compound | Structure | ¹H NMR (500 MHz, CDCl₃, ppm) |
|---|---|---|
| 3-methyl-5-tert-butyl-1,2-phenylene di(2-naphthoate) | 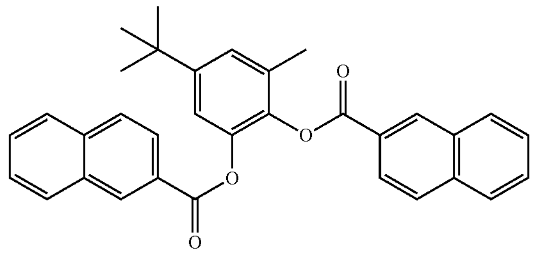 [SMILES: Cc1cc(C(C)(C)C)cc(OC(=O)c2ccc3ccccc3c2)c1OC(=O)c1ccc2ccccc2c1] | |
| 3-methyl-5-tert-butyl-1,2-phenylene di(4-ethylbenzoate) | 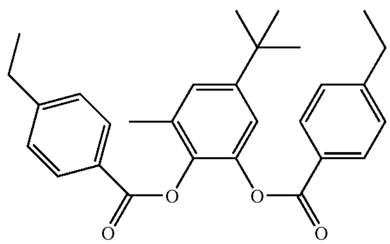 [SMILES: CCc1ccc(C(=O)Oc2cc(C(C)(C)C)cc(C)c2OC(=O)c2ccc(CC)cc2)cc1] | δ 7.99 (d, 2H), 7.95 (d, 2H), 7.18 (m, 6H), 2.66 (m, 4H), 2.26 (s, 3H), 1.34 (s, 9H), 1.21 (m, 6H) |
| 3-methyl-5-tert-butyl-1,2-phenylene di(4-ethoxybenzoate) | 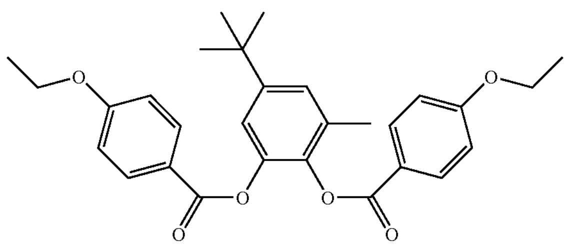 [SMILES: CCOc1ccc(C(=O)Oc2cc(C(C)(C)C)cc(C)c2OC(=O)c2ccc(OCC)cc2)cc1] | δ 8.02 (d, 2H), 7.97 (d, 2H), 7.17 (m, 2H), 6.83 (d, 2H), 6.79 (d, 2H), 4.04 (m, 4H), 2.25 (s, 3H), 1.41 (m, 6H), 1.33 (s, 9H) |
| 3-methyl-5-(2,4,4-trimethylpentan-2-yl)-1,2-phenylene dibenzoate 2,4,4-trimethylpentan-2-yl | 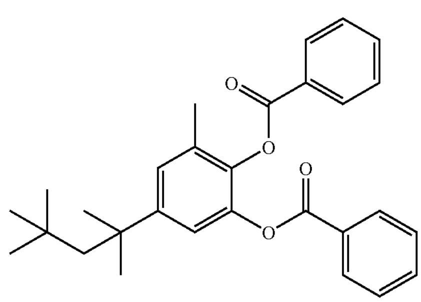 [SMILES: Cc1cc(C(C)(C)CC(C)(C)C)cc(OC(=O)c2ccccc2)c1OC(=O)c1ccccc1] | δ 8.09 (d, 2H), 8.02 (d, 2H), 7.50 (m, 2H), 7.38 (t, 2H), 7.33 (t, 2H), 7.19 (s, 2H), 2.27 (s, 3H), 1.75 (s, 2H), 1.40 (s, 6H), 0.81 (s, 9H) |
| 3-methyl-5-tert-butyl-1,2-phenylene di(4-fluorobenzoate) | 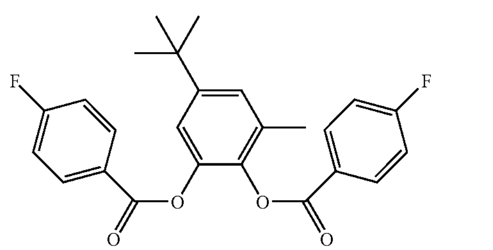 [SMILES: Cc1cc(C(C)(C)C)cc(OC(=O)c2ccc(F)cc2)c1OC(=O)c1ccc(F)cc1] | δ 8.07 (m, 4H), 7.21 (s, 1H), 7.17 (s, 1H), 7.04 (m, 4H), 2.27 (s, 3H), 1.34 (s, 9H) |

TABLE 1-continued

| Compound | Structure | $^1$H NMR (500 MHz, CDCl$_3$, ppm) |
|---|---|---|
| 3-fluoro-1,2-phenylene di(4-chlorobenzoate) | 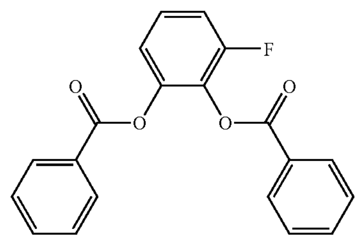 [SMILES: O=C(Oc1cccc(F)c1OC(=O)c1ccccc1)c1ccccc1] | δ 8.10 (d, 2H), 8.07 (d, 2H), 7.56 (m, 2H), 7.40 (m, 4H), 7.31 (m, 1H), 7.18 (m, 2H) |
| 4-tert-butyl-1,2-phenylene di(2-methylbenzoate) | 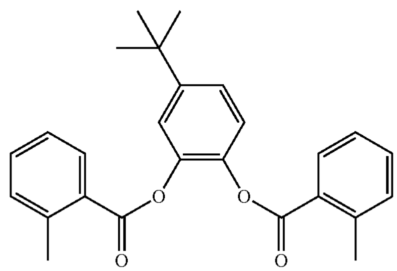 [SMILES: Cc1ccccc1C(=O)Oc1ccc(C(C)(C)C)cc1OC(=O)c1ccccc1C] | δ 8.04 (d, 1H), 8.00 (d, 1H), 7.39 (m, 3H), 7.34 (m, 1H), 7.28 (d, 1H), 7.22 (m, 2H), 7.17 (m, 2H), 2.57 (s, 6H), 1.36 (s, 9H) |
| 4-methyl-1,2-phenylene di(2-methylbenzoate) | 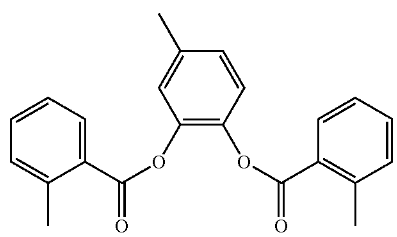 [SMILES: Cc1ccc(OC(=O)c2ccccc2C)c(OC(=O)c2ccccc2C)c1] | δ 8.01 (d, 2H), 7.39 (m, 2H), 7.22 (m, 3H), 7.15 (m, 4H), 2.57 (s, 3H), 2.56 (s, 3H), 2.42 (s, 3H) |
| 4-tert-butyl-1,2-phenylene di(2,4,6-trimethylbenzoate) | 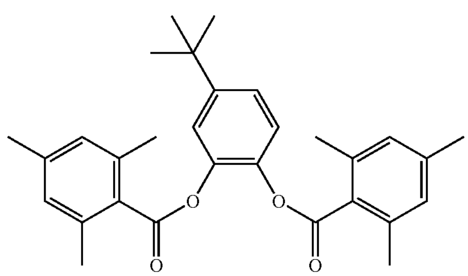 | δ 7.36 (s, 3H), 6.83 (s, 4H), 2.29 (s, 6H), 2.26 (s, 12H), 1.34 (s, 9H) |
| 4-methyl-1,2-phenylene di(2,4,6-trimethylbenzoate) | 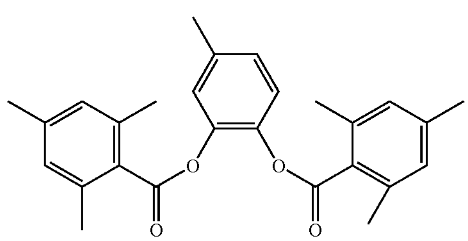 | δ 7.29 (d, 1H), 7.22 (m, 1H), 7.14 (m, 1H), 6.83 (m, 3H), 2.42 (s, 3H), 2.29 (s, 6H), 2.25 (s, 6H), 2.24 (s, 6H) |

TABLE 1-continued

| Compound | Structure | $^1$H NMR (500 MHz, CDCl$_3$, ppm) |
|---|---|---|
| 1,2-phenylene di(2,4,6-trimethylbenzoate) | 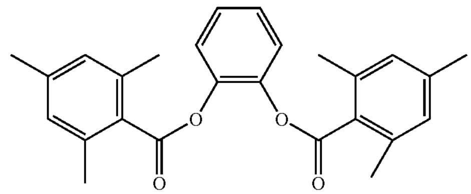 | δ 7.43 (m, 2H), 7.35 (m, 2H), 6.84 (s, 4H), 2.29 (s, 6H), 2.25 (s, 12H). |

2. Procatalyst Preparation

In a 75 mL glass vessel fitted with a overhead stirrer and purged with nitrogen, three grams of MagTi are suspended in 60 mL 50/50 vol/vol TiCl$_4$/chlorobenzene. The internal electron donor (either IED1 or IED 2), dissolved in chlorobenzene, is then added via syringe. The suspension is heated in 15 minutes to the tabulated temperature and maintained at this temperature for 60 minutes with stirring (250 rpm). The solid is isolated by filtration and then re-suspended in 50/50 TiCl$_4$/chlorobenzene. An internal electron donor is optionally added to the suspension. The suspension is heated to 115° C. in fifteen minutes and then maintained at this temperature for 30 minutes with stirring (250 rpm). The chlorination step is repeated a third time, but without addition of internal electron donor. The resulting procatalyst is isolated by filtration, rinsed three times in room temperature isooctane and dried under nitrogen flow for 2 hours. Properties for resultant procatalyst compositions are provided in Table 2 below.

TABLE 2

| Sample | Electron Donor (IED) | IED in 1$^{st}$ Chlorination Step, mmol | IED in 2$^{nd}$ Chlorination Step, mmol | Temperature, of 1st Chlorination Step, ° C. | % wt. Ti | % wt. OEt | % wt. IED | % wt. EB |
|---|---|---|---|---|---|---|---|---|
| C1 | IED1 | 3.14 | 0 | 115 | 3.32 | 0.30 | 14.9 | 4.6 |
| Ex 1 | IED1 | 3.14 | 0 | 100 | 3.13 | 0.21 | 23.2 | 1.5 |
| C2 | IED2 | 2.42 | 2.42 | 115 | 2.97 | 0.14 | 9.7 | 2.7 |
| Ex 2 | IED2 | 2.42 | 2.42 | 100 | 2.81 | 0.10 | 10.6 | 2.3 |

EB = ethyl benzoate
OEt = ethoxide
Wt % = based on total weight of the procatalyst

3. Polymerization

Polymerizations are conducted in a one-gallon stainless steel autoclave, fitted with a 2 L drop pot. The reactor is prepared for polymerization by heating the reactor to 140° C., purging with nitrogen, cooling the reactor to 40° C. and then purging with hydrogen. The reactor is then filled with 300 g liquid propylene, heated to 50° C., cooled to 25° C. and then emptied. Propylene (1375 g) and 6000 scc hydrogen are fed into the reactor. The stir motor is set to 1000 rpm and the temperature is raised to 62° C. The catalyst components are then injected as a premixed solution of the external electron donor, triethylaluminum and the catalyst slurry (premixed together for 20 minutes). The reactor is controlled to 67° C. and maintained at this temperature for the remainder of the 1 hour of polymerization. Specific run conditions such as catalyst load, donor load and hydrogen level are summarized in the data tables.

Table 3 summarizes the performance data for procatalyst compositions prepared as described above.

TABLE 3

Procatalyst Selectivity for IED and a Lowered First Halogenation Temperature

| Sample | Electron Donor (IED) | IED in 1$^{st}$ Chlorination Step, mmol | IED in 2$^{nd}$ Chlorination Step, mmol* | Temperature, of 1$^{st}$ Chlorination Step, ° C. | g PP | BD g/cc | MFR g/10 min | XS % wt. |
|---|---|---|---|---|---|---|---|---|
| C1 | IED1 | 3.14 | 0 | 115 | 267 | 0.291 | 4.6 | 1.3 |
| Ex 1 | IED1 | 3.14 | 0 | 100 | 251 | 0.297 | 4.9 | 1.0 |

TABLE 3-continued

Procatalyst Selectivity for IED and a Lowered First Halogenation Temperature

| Sample | Electron Donor (IED) | IED in 1st Chlorination Step, mmol | IED in 2nd Chlorination Step, mmol* | Temperature, of 1st Chlorination Step, °C. | g PP | BD g/cc | MFR g/10 min | XS % wt. |
|---|---|---|---|---|---|---|---|---|
| C2 | IED2 | 2.42 | 2.42 | 115 | 211 | 0.349 | 3.3 | 2.1 |
| Ex 2 | IED2 | 2.42 | 2.42 | 100 | 188 | 0.347 | 2.4 | 1.5 |

*2nd chlorination temp = 115° C.
Polymerizations Conditions: 5 mg catalyst, 83 μmol dicyclopentyldimethoxysilane, 2.3 mmol triethylaluminum.

Table 4 below shows the performance data for procatalyst compositions prepared with a low first halogenation temperature and a high second halogenation temperature.

TABLE 4

| Sample | Donor | IED added to First Chlorination, mmol | First Chlorination Temperature, °C. | Second Chlorination Temperature, °C. | Third Chlorination Temperature, °C. | g PP | BD g/cc | MFR g/10 min | XS % wt |
|---|---|---|---|---|---|---|---|---|---|
| Ex4 | IED1 | 2.42 | 100 | 115 | 115 | 287 | 0.275 | 5.9 | 2.3 |
| Ex5 | IED1 | 2.42 | 100 | 130 | 115 | 342 | 0.294 | 4.3 | 1.7 |
| Ex6 | IED1 | 2.42 | 100 | 115 | 130 | 356 | 0.305 | 5.2 | 2.1 |
| Ex7 | IED1 | 2.42 | 100 | 130 | 130 | 331 | 0.323 | 5.2 | 1.6 |

Polymerizations Conditions: 5 mg catalyst, 83 μmol dicyclopentyldimethoxysilane, 2.3 mmol triethylaluminum.

Table 5 below shows that the polymer bulk density increases as procatalyst precursor size decreases. Surprisingly, the quantity of polymer fines is unchanged. The quantity of polymer fines typically increases when smaller precursors are used.

TABLE 5

| Sample | Donor | Catalyst Precursor Size (microns) | Polymer Bulk Density (g/cm3) | Melt Flow (dg/min) | Xylene solubles (wt %) | Productivity (kg/g) | Average Particle Size (inch) | Polymer Fines (<250 micron) |
|---|---|---|---|---|---|---|---|---|
| C3 | IED1 | 28.4 | 0.231 | 1.2 | 3.2 | 57.8 | 0.051 | 0.95 |
| Ex8 | IED1 | 23.3 | 0.288 | 1.0 | 2.8 | 55.4 | 0.039 | 0.7 |

Table 6 below shows that the polymer bulk density increase is additive when a smaller procatalyst is prepared with a low first halogenation temperature and high second and third halogenation temperatures.

TABLE 6

| Sample | Donor | Procat D50, μm | IED added to 1st Chlor, mmol | IED added to 2nd Chlor, mmol | 1st Chlor Temp., °C. | 2nd Chlor Temp., °C. | 3rd Chlor Temp., °C. | g PP | BD g/cc | MFR | % wt XS |
|---|---|---|---|---|---|---|---|---|---|---|---|
| Ex9 | IED1 | 27 | 2.18 | 1.21 | 100 | 130 | 130 | 282 | 0.381 | 6.3 | 1.4 |
| Ex10 | IED1 | 23 | 2.18 | 1.21 | 100 | 130 | 130 | 252 | 0.394 | 6.1 | 1.3 |

Polymerizations Conditions: 5 mg catalyst, 83 μmol dicyclopentyldimethoxysilane, 2.3 mmol triethylaluminum.

It is specifically intended that the present invention not be limited to the embodiments and illustrations contained herein, but include modified forms of those embodiments including portions of the embodiments and combinations of elements of different embodiments as come within the scope of the following claims.

The invention claimed is:

1. A process comprising: halogenating a procatalyst precursor in the presence of a substituted phenylene aromatic diester at a temperature from about 90° C. to less than or equal to 100° C., wherein the substituted phenylene aromatic diester is 5-tert-butyl-3-methyl-1,2-phenylene dibenzoate, to form a procatalyst composition with ethyl benzoate from 0 wt% to less than 2.3 wt %.

2. The process of claim 1 comprising contacting, under polymerization conditions, the procatalyst composition, a cocatalyst, and optionally an external electron donor with propylene and optionally one or more olefins; and forming a propylene-based polymer having less than 2.5 wt % xylene solubles.

3. A process comprising:

first halogenating a procatalyst precursor in the presence of a substituted phenylene aromatic diester at a temperature less than 115° C. to form a procatalyst intermediate, wherein the substituted phenylene aromatic diester is selected from the group consisting of 5-tert-butyl-3-methyl-1,2-phenylene dibenzoate and 4-tert-butyl-1,2phenylene dibenzoate;

second halogenating the procatalyst intermediate at a temperature greater than or equal to 115° C.;

to form a procatalyst composition with a bulk density index from about 0.28 to about 0.5.

4. The process of claim 3 comprising preparing particles of the procatalyst precursor, the particles having a D50 from about 10 μm to about 25μm.

5. The process of claim 3 comprising first halogenating the procatalyst precursor at a temperature from 90° C. to less than or equal to 100° C. and second halogenating the procatalyst intermediate at a second temperature greater than or equal to 115° C.

6. The process of claim 3 comprising second halogenating the procatalyst intermediate in the presence of a substituted phenylene aromatic diester.

7. The process of claim 3 comprising third halogenating the procatalyst intermediate at a third temperature greater than or equal to 115° C.

8. The process of claim 3 comprising contacting, under polymerization conditions, the procatalyst composition, a cocatalyst, and an external electron donor with propylene and optionally one or more olefins; and forming particles of a propylenebased polymer having a bulk density from about 0.28 g/cc to about 0.5 g/cc as measured in accordance with ASTM D 1895B.

9. The process of claim 3 wherein the substituted phenylene aromatic diester is5-tert-butyl-3-methyl-1,2-phenylene dibenzoate.

10. The process of claim 3 wherein the substituted phenylene aromatic diester is 4-tert-butyl-1,2-phenylene dibenzoate.

* * * * *